United States Patent
Ono et al.

(10) Patent No.: US 11,679,083 B2
(45) Date of Patent: Jun. 20, 2023

(54) METHOD FOR PRODUCING FREEZE-DRIED FORMULATION

(71) Applicant: FUJIFILM Toyama Chemical Co., Ltd., Chuo-ku (JP)

(72) Inventors: Makoto Ono, Toyama (JP); Takafumi Hirota, Toyama (JP); Iori Mizogaki, Toyama (JP)

(73) Assignee: FUJIFILM Toyama Chemical Co., Ltd., Chuo-ku (JP)

( * ) Notice: Subject to any disclaimer, the term of this patent is extended or adjusted under 35 U.S.C. 154(b) by 393 days.

(21) Appl. No.: 16/958,469

(22) PCT Filed: Dec. 14, 2018

(86) PCT No.: PCT/JP2018/046126
§ 371 (c)(1),
(2) Date: Jun. 26, 2020

(87) PCT Pub. No.: WO2019/131223
PCT Pub. Date: Jul. 4, 2019

(65) Prior Publication Data
US 2021/0059947 A1 Mar. 4, 2021

(30) Foreign Application Priority Data

Dec. 28, 2017 (JP) .............................. JP2017-253576

(51) Int. Cl.
*A61K 9/19* (2006.01)
*A61K 9/00* (2006.01)
*A61K 31/4965* (2006.01)

(52) U.S. Cl.
CPC .............. *A61K 9/19* (2013.01); *A61K 9/0019* (2013.01); *A61K 31/4965* (2013.01)

(58) Field of Classification Search
CPC ................ A61K 9/19; A61K 31/4965
See application file for complete search history.

(56) References Cited

U.S. PATENT DOCUMENTS

| | | |
|---|---|---|
| 6,770,678 B1 | 8/2004 | Kurz et al. |
| 2002/0013316 A1 | 1/2002 | Furuta et al. |
| 2006/0247203 A1 | 11/2006 | Kato et al. |
| 2013/0217708 A1 | 8/2013 | Takakura et al. |
| 2013/0274472 A1 * | 10/2013 | Takakura ............. C07D 241/24 544/406 |

FOREIGN PATENT DOCUMENTS

| | | | |
|---|---|---|---|
| CA | 2 361 237 A1 | 8/2000 | |
| CA | 2361237 A1 * | 8/2013 | ............... A61K 9/19 |
| JP | 2002-535089 A | 10/2002 | |
| JP | 2008-231067 A | 10/2008 | |
| JP | 4753717 B2 | 8/2011 | |
| JP | 2012-214525 A | 11/2012 | |
| WO | WO 00/10569 A1 | 3/2000 | |
| WO | WO 2012/043696 A1 | 4/2012 | |
| WO | WO 2012/043700 A1 | 4/2012 | |
| WO | WO 2018/003946 A1 | 1/2018 | |

OTHER PUBLICATIONS

International Search Report dated Feb. 26, 2019 in PCT/JP2018/046126 filed on Dec. 14, 2018, 1 page.
Kawasaki, "Design of Lyophilization Processes," Journal of Japan Society of Pharmaceutical Machinery and Engineering, 2015, vol. 24, No. 2, pp. 39-51.

\* cited by examiner

*Primary Examiner* — Michael B. Pallay
(74) *Attorney, Agent, or Firm* — Oblon, McClelland, Maier & Neustadt, L.L.P.

(57) ABSTRACT

This method for producing a freeze-dried formulation including an amorphous form of 6-fluoro-3-hydroxy-2-pyrazinecarboxamide sodium salt is useful as a method for producing a freeze-dried formulation having uniform quality.

12 Claims, 1 Drawing Sheet

METHOD FOR PRODUCING FREEZE-DRIED FORMULATION

TECHNICAL FIELD

The present invention relates to a method of producing a lyophilized preparation containing amorphous sodium salt of 6-fluoro-3-hydroxy-2-pyrazine carboxamide (hereinafter, also referred to as "Compound A").

BACKGROUND ART

Recently, there has been a fear of the pandemic of highly-virulent influenza. For example, oseltamivir, zanamivir, laninamivir, and amantadine are currently used as influenza drugs. However, these drugs have a disadvantage of being unable to be administered to patients with difficulty of oral intake.

The Compound A or its salt has an excellent antiviral activity, and is useful as a therapeutic drug for virus infection (Patent Literature 1). There have been reports on an injectable solution of sodium salt and meglumine salt of Compound A (Patent Literatures 2 and 3).

As a method of producing an injectable solution, for example, a lyophilization-based method is known.

A general lyophilization process includes a freezing step, a primary drying step, and a secondary drying step. The freezing step is one of the important steps which determine the product quality.

In the freezing step, water does not freeze spontaneously and maintains a supercooled state. When the supercooling degree is increased due to a certain cause, the freezing start temperature is decreased and the size of ice crystals formed by quick freezing becomes smaller. The small size of ice crystals does not allow water vapor to be efficiently sublimated in the primary drying step, thereby causing melting and foaming of the frozen product and forming of a product having an abnormal appearance, resulting in non-uniform-quality products.

In order to realize uniform quality of products, it is preferable to control the freezing step and suppress supercooling.

In this regard, lyophilization is easily influenced by a difference in scale between a test device and a production device. It is due to the fact that the test and production devices are not necessarily identical in shape and material quality, and cooling and heating transfer efficiencies vary depending on differences in scale (Non Patent Literature 1). It is desired that the method of suppressing supercooling has suitability for scale-up that can be achieved in the production device, similarly to the test device.

As the existing method of controlling the freezing step, a technique such as pre-cooling, gradually-cooling, annealing or addition of additives has been examined (Patent Literatures 4, 5, and 6). However, any method is not necessarily satisfactory in terms of certainty of control, simplicity of operation, and suitability for scale up.

CITATION LIST

Patent Literatures

PATENT LITERATURE 1: International Publication No. 00/10569
PATENT LITERATURE 2: International Publication No. 2012/043696
PATENT LITERATURE 3: International Publication No. 2012/043700
PATENT LITERATURE 4: Japanese Patent Application Laid-Open No. 2008/231067
PATENT LITERATURE 5: Japanese Patent No. 4753717
PATENT LITERATURE 6: Japanese Patent Application Laid-Open No. 2012-214525

Non Patent Literature

NON PATENT LITERATURE 1: Journal of Japan Society of Pharmaceutical Machinery and Engineering, Vol. 24, No. 2, pp. 39-51, 2015

SUMMARY OF INVENTION

Technical Problem

There is a need for a scalable production method of a uniform-quality of lyophilized preparation containing Compound A or its salt.

Solution to Problem

Under such circumstances, the present inventors have dedicated to repetitive studies, and consequently found a scalable production method of a uniform-quality lyophilized preparation containing a sodium salt of Compound A (hereinafter also referred to as "Salt A").

The present inventors have found that the freezing step affects the variation in appearance of the lyophilized preparation. Then, they have found that a whole solution in a state of once being heated is quickly cooled so as to facilitate convective flow associated with a temperature difference between a part closer to and another part distant from a cooling source (a large temperature difference results in an increase of a difference in density of water, and thus a convective flow easily occurs), thereby cooling the whole solution quickly and uniformly. In other words, they have found that it is possible to freeze water with little supercooling.

Further, the present inventors have dedicated to repetitive studies. As a result, they have found that
(1) the temperature of an aqueous solution of Salt A before cooling (hereinafter, also referred to as "cooling start temperature") is adjusted to 20° C. or more, cooled within a certain period of time, and lyophilized, thereby producing a lyophilized preparation containing amorphous Salt A,
(2) the lyophilized preparation obtained has a uniform quality such that the variation in appearance is very small, and
(3) it is possible to easily scale up the freezing step; and have completed the present invention.

The present invention provides the followings.
[1] A method of producing a lyophilized preparation containing amorphous sodium salt of 6-fluoro-3-hydroxy-2-pyrazine carboxamide, including the steps of:
(1) adjusting the temperature of an aqueous solution containing a sodium salt of 6-fluoro-3-hydroxy-2-pyrazine carboxamide to 20° C. or more;
(2) cooling the aqueous solution obtained in the step (1) to −40° C. or less within 1 hour to produce a frozen product; and
(3) lyophilizing the frozen product obtained in the step (2).

[2] The production method according to [1], wherein the temperature in the step (1) is in a range of 20° C. or more and less than 30° C.

[3] The production method according to [1], wherein the temperature in the step (1) is in a range of 30° C. or more and less than 40° C.

[4] The production method according to [1], wherein the temperature in the step (1) is in a range of 40° C. or more and less than 50° C.

[5] The production method according to [1], wherein the temperature in the step (1) is a range of 50° C. or more and less than 60° C.

[6] The production method according to [1], wherein the temperature in the step (1) is in a range of 60° C. or more and less than 70° C.

[7] A method of producing a lyophilized preparation containing amorphous sodium salt of 6-fluoro-3-hydroxy-2-pyrazine carboxamide, including the steps of:

(1) adjusting the temperature of an aqueous solution containing a sodium salt of 6-fluoro-3-hydroxy-2-pyrazine carboxamide to 40° C. or more;

(2) cooling the aqueous solution obtained in the step (1) to −40° C. or less within 3 hours to produce a frozen product; and (3) lyophilizing the frozen product obtained in the step (2).

[8] The production method according to [7], wherein the temperature in the step (1) is in a range of 40° C. or more and less than 50° C.

[9] The production method according to [7], wherein the temperature in the step (1) is in a range of 50° C. or more and less than 60° C.

[10] The production method according to [7], wherein the temperature in the step (1) is in a range of 60° C. or more and less than 70° C.

[11] The production method according to any one of [1] to [10], wherein the temperature of the frozen product during sublimation of water in the primary drying step (3) is in a range of −30° C. or more and less than 0° C., and the vacuum degree (absolute pressure) is in a range of 15 Pa or more and less than 25 Pa.

[12] The production method according to any one of [1] to [10], wherein the temperature of the frozen product during sublimation of water in the primary drying in the step (3) is in a range of −40° C. or more and less than −15° C.

Advantageous Effect of Invention

The method of producing a lyophilized preparation containing amorphous Salt A of the present invention can perform scale-up and is useful as a method of producing a uniform quality of lyophilized preparation.

DESCRIPTION OF EMBODIMENT

Hereinafter, the present invention will be described in detail.

Compound A can be produced by, for example, the method described in Patent Literature 1. In this regard, 6-fluoro-3-oxo-3,4-dihydro-2-pyrazine carboxamide (i.e., a tautomer) is present in Compound A. The present invention also includes this compound.

The method of producing a lyophilized preparation containing amorphous Salt A of the present invention will be described below.

Production Method 1

<Step (1)>

This step is a step of adjusting the temperature of an aqueous solution containing Salt A to 20° C. or more.

The aqueous solution containing Salt A can be obtained by, for example, mixing Compound A, a base, and water.

The amount of water may be 10 to 100 times the amount (v/w) of Compound A and is preferably 10 to 50 times the amount (v/w).

Examples of bases include sodium hydroxide, sodium hydrogen carbonate, and sodium carbonate.

The amount of the base may be an amount in which the pH of the aqueous solution is from 4 to 10, and is preferably an amount in which the pH of the aqueous solution is from 6.5 to 9.

The aqueous solution containing Salt A can be obtained by an alternative method of mixing an aqueous solution of sodium hydroxide, sodium hydrogen carbonate or sodium carbonate with Compound A.

Further, the aqueous solution containing Salt A can be obtained by an alternative method of dissolving Salt A in water.

It is preferable to obtain an aqueous solution containing Salt A in a state that a container which can be sealed later is filled with it. The aqueous solution containing salt A with which a container which can be sealed later was filled can be obtained by filling a sealable container with the separately prepared aqueous solution containing Salt A. It can also be obtained by dissolving Compound A, a base and water in a container which can be sealed later.

Examples of the containers sealable later include vials, ampoules, syringes, cartridges, etc. It is preferable that the inner surface of the container is silicone-coated. Since the inner surface of the container is silicone-coated, cracking of the container during production of the lyophilized preparation can be suppressed.

As one embodiment of the present invention, the cooling start temperature is preferably 20° C. or more and more preferably in a range of 20° C. or more and less than 30° C.

As another embodiment of the present invention, the cooling start temperature is preferably 20° C. or more and more preferably in a range of 30° C. or more and less than 40° C.

As still another embodiment of the present invention, the cooling start temperature is preferably 20° C. or more and more preferably in a range of 40° C. or more and less than 50° C.

Further, as still another embodiment of the present invention, the cooling start temperature is preferably 20° C. or more and more preferably in a range of 50° C. or more and less than 60° C.

Further, as still another embodiment of the present invention, the cooling start temperature is preferably 20° C. or more and more preferably in a range of 60° C. or more and less than 70° C.

<Step (2)>

This step is a step of cooling the aqueous solution obtained in the step (1) to −40° C. or less to produce a frozen product.

The time required to cool the aqueous solution to −40° C. or less is not particularly limited and is preferably within 1 hour.

In another embodiment of the present invention, when the cooling start temperature is in a range of 40° C. or more and less than 50° C., when the cooling start temperature is in a range of 50° C. or more and less than 60° C., or when the cooling start temperature is in a range of 60° C. or more and less than 70° C., the time required to cool the aqueous solution to −40° C. or less is preferably within 3 hours, more preferably within 2 hours, and still more preferably within 1 hour.

The aqueous solution may be cooled to −40° C. or less. Specific examples include −40° C. or less, −41° C. or less, −42° C. or less, −43° C. or less, −44° C. or less, −45° C. or less, −46° C. or less, and −47° C. or less. It is preferable to cool it to a range of −40° C. or less and −70° C. or more, it is more preferable to cool it to a range of −45° C. or less and −70° C. or more.

Cooling rate is not particularly limited but 28° C./h or more is preferred, 55° C./h or more is more preferred, and 85° C./h or more is furthermore preferred.

<Step (3)>

This step is a step of lyophilizing the frozen product obtained in the step (2).

The step may be performed in accordance with the lyophilization method, which is usually performed. For example, it can be performed by two steps of primary and secondary drying steps.

The primary drying step is performed by keeping the frozen product at an eutectic point or less under reduced pressure. Since a decrease in temperature is accompanied by sublimation of water from the frozen product, the preset temperature of a lyophilization device may be set to the eutectic point or more.

During sublimation of water, the temperature of the frozen product is maintained almost at a constant level (hereinafter, also referred to as "the temperature of the frozen product during sublimation of water").

The temperature of the frozen product during sublimation of water may be −40° C. or more and less than 0° C. and is preferably −30° C. or more and less than 0° C.

In another embodiment of the present invention, the temperature of the frozen product during sublimation of water may be −40° C. or more and less than 0° C., preferably −40° C. or more and less than −15° C., and more preferably −35° C. or more and less than −20° C.

The vacuum degree (absolute pressure) in the primary drying step is not particularly limited, and it may be 50 Pa or less, and it is preferably 30 Pa or less and more preferably in a range of 15 Pa or more and less than 25 Pa.

In another embodiment of the present invention, the vacuum degree (absolute pressure) in the primary drying step is not particularly limited, and it may be less than 25 Pa, and it is preferably 20 Pa or less and more preferably 15 Pa or less.

The temperature is gradually decreased with a decrease of the sublimating water. This results in increasing of the temperature of the frozen product, and the temperature of the frozen product becomes nearly identical to the preset temperature. Usually, this point of time is determined to be the completion of the primary drying step.

Subsequently, the secondary drying step is performed.

The secondary drying step is performed at 20° C. or more, and the temperature is preferably from 30 to 60° C. and more preferably from 40 to 50° C.

In the secondary drying step, it is preferable to increase the vacuum degree in order to promote the elimination of water. The vacuum degree (absolute pressure) may be from 0.5 to 50 Pa, and is preferably from 0.5 to 5 Pa.

The secondary drying step may be performed until when the temperature of the product becomes nearly identical to the preset temperature and no change of the product temperature is observed.

The lyophilized preparation containing amorphous Salt A produced by this production method has a very small variation in appearance. In other words, this production method allows for production of a uniform quality of lyophilized preparation containing amorphous Salt A.

To the lyophilized preparation containing amorphous Salt A of the present invention, additives for improving solubility and/or appearance can be added. Examples of additives include amino acids, polyethers, saccharides, sugar alcohols, salts, urea, ethylurea, creatinine, nicotinamide, trometamol, purified soybean lecithin, ovalbumin, bovine serum albumin, and polysorbate 80. One kind or two or more kinds of these additives can be mixed and used.

Examples of amino acids include glycine, L-alanine, L-phenylalanine, L-valine, L-leucine, L-isoleucine, taurine, DL-methionine, L-threonine, L-glutamine, monosodium L-glutamate, acetyl tryptophan, and L-histidine. Preferred are L-alanine, L-phenylalanine, L-valine, L-leucine, L-isoleucine, taurine, DL-methionine, L-glutamine, and L-histidine. More preferred are L-leucine, L-isoleucine, and L-valine.

Examples of polyethers include polyethylene glycol 300, polyethylene glycol 400, polyethylene glycol 600, and polyethylene glycol 4000. Preferred is polyethylene glycol 400.

Examples of saccharides include trehalose, maltose, glucose, lactose, sucrose, fructose, dextran, and cyclodextrin. Preferred is dextran 40.

Examples of sugar alcohols include D-sorbitol, xylitol, inositol, isomaltose, and D-mannitol.

Examples of salts include sodium acetate, sodium lactate, disodium L-tartrate, sodium citrate, sodium salicylate, sodium benzoate, and sodium caprylate.

Examples of preferable additives include amino acids, polyethers, saccharides, urea, and polysorbate 80.

To the preparation of the present invention, an osmo-regulator, a pH regulator, a buffer, a solubilizer, a stabilizer, a surfactant, a soothing agent and/or a preservative, which are usually used, may be added, if necessary.

Examples of osmo-regulators include sodium chloride, glycerin, and propylene glycol.

Examples of pH regulators and/or buffers include acids such as hydrochloric acid, phosphoric acid, sulfuric acid, methanesulfonic acid, acetic acid, lactic acid, maleic acid, citric acid, tartaric acid, ascorbic acid, and benzoic acid; salts such as sodium hydrogen carbonate, sodium carbonate, sodium dihydrogen phosphate, potassium dihydrogen phosphate, disodium hydrogenphosphate, dipotassium hydrogenphosphate, trisodium phosphate, disodium citrate, sodium deoxycholate, and sodium sulfite; and bases such as sodium hydroxide, trometamol, monoethanolamine, diethanolamine, triethanolamine, L-arginine, and L-lysine.

Examples of solubilizers include macrogol and purified soybean lecithin.

Examples of stabilizers include sodium bisulfite, sodium pyrosulfite, potassium pyrosulfite, sodium pyrophosphate, sodium thiosulfate, sodium metasulfobenzoate, sodium formaldehyde sulfoxylate, ethylenediamine, edetate sodium, thioglycolic acid, sodium gluconate, monopotassium L-glutamate, L-lysine-L-glutamate, sodium chondroitin sulfate, albumin, L-asparatic acid, L-cysteine, and dibutyl hydroxy toluene.

Examples of surfactants include sorbitan fatty acid ester, polyoxyethylene hydrogenated castor oil, polyoxyethylene sorbitan monolaurate, polyoxyethylene polyoxypropylene glycol, and polysorbate.

Examples of soothing agents include lidocaine, procaine, meprylcaine, and benzyl alcohol.

Examples of preservatives include cresol, phenol, methyl parahydroxybenzoate, ethyl parahydroxybenzoate, benzalkonium chloride, and benzethonium chloride.

The dosage amount of the active substance in the lyophilized preparation obtained by the production method of the present invention may be appropriately determined depending on the dosage regimen, the age and gender of patients, the form of disease, other conditions or the like. Usually, the active substance may be administered to an adult in an amount of 0.1-200 mg/kg per day.

The containing amount of Compound A in the lyophilized preparation obtained by the production method of the present invention is from 10 to 6000 mg, and preferably from 100 to 2000 mg.

The amount of additives for improving solubility and/or appearance, which are blended into the lyophilized preparation obtained by the production method of the present invention, is from 0 to 100% (w/w), and preferably from 0 to 50% (w/w) relative to Compound A.

EXAMPLES

Hereinafter, the present invention will be described with reference to Examples and Test examples, however the present invention is not limited thereto.
<Method of Confirming Quality (Appearance) of Lyophilized Preparation>

The appearances of all lyophilized preparations (excluding the vial after the measurement of the product temperature) were visually observed and determined according to the following two stages:

good-appearance product: a lyophilized preparation having a yellow to light yellow appearance and showing no white part; and poor-appearance product: a lyophilized preparation showing a white part.

The yield rate was calculated by the following equation:

Yield rate (%)=(the number of good-appearance products/(the number of good-appearance products+the number of poor-appearance products))×100

Example 1

In 350 mL of water for injection, 42.19 g of Compound A was suspended under stirring. Separately, 10.66 g of sodium hydroxide was dissolved in 250 mL of water for injection under stirring. The sodium hydroxide solution was added to the suspension of Compound A. After confirming the dissolution under stirring, 0.2 mol/kg of the sodium hydroxide solution was added to adjust the pH to 8.0. Water for injection was added to raise the total volume to 700 mL, and the resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 100%

Lyophilization Method
1. The shelf temperature was adjusted to 50° C. and the vial was kept at this temperature for 180 minutes.
2. The shelf temperature was reduced to −47° C. over a period of 53 minutes so as to freeze the content.
3. The vacuum degree (absolute pressure) was set up to 20 Pa and the shelf temperature was increased to 25° C. The vial was kept at this pressure and temperature for 35 hours. The temperature of the frozen product during sublimation of water was −13.2 to −3.3° C.
4. The shelf temperature was increased to 50° C. The vial was kept at this temperature and a vacuum degree (absolute pressure) of 1.1 Pa for 24 hours.

In the Examples, the shelf temperature means the shelf temperature of the lyophilization machine.

Example 2

In 1450 g of water for injection, 181 g of Compound A was suspended under stirring. Separately, 46 g of sodium hydroxide was dissolved in 1100 g of water for injection under stirring. The sodium hydroxide solution was added to the suspension of Compound A. After confirming the dissolution under stirring, 0.2 mol/kg of the sodium hydroxide solution was added to adjust the pH to 7.6. Water for injection was added to raise the total volume to 3 L, and then 750 mL of the resulting mixture was fractionated. Thereto, 0.2 mol/kg of the sodium hydroxide solution was added to adjust the pH to 8.0. The resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 100%

Lyophilization Method
1. The shelf temperature was adjusted to 40° C. and the vial was kept at this temperature for 180 minutes.
2. The shelf temperature was reduced to −47° C. over a period of 53 minutes so as to freeze the content.
3. The vacuum degree (absolute pressure) was set up to 20 Pa and the shelf temperature was increased to 25° C. The vial was kept at this pressure and temperature for 15 hours. The temperature of the frozen product during sublimation of water was −13.7 to −6.0° C.
4. The shelf temperature was increased to 50° C. The vial was kept at this temperature and a vacuum degree (absolute pressure) of 1.1 Pa for 22 hours.

Example 3

In 350 mL of water for injection, 42.16 g of Compound A was suspended under stirring. Separately, 10.65 g of sodium hydroxide was dissolved in 250 mL of water for injection under stirring. The sodium hydroxide solution was added to the suspension of Compound A. After confirming the dissolution under stirring, 0.2 mol/kg of the sodium hydroxide solution was added to adjust the pH to 8.0. Water for injection was added to raise the total volume to 700 mL, and the resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 100%

Lyophilization Method

1. The shelf temperature was adjusted to 30° C. and the vial was kept at this temperature for 180 minutes.
2. The shelf temperature was reduced to −47° C. over a period of 53 minutes so as to freeze the content.
3. The vacuum degree (absolute pressure) was set up to 20 Pa and the shelf temperature was increased to 25° C. The vial was kept at this pressure and temperature for 35 hours. The temperature of the frozen product during sublimation of water was −6.1° C.
4. The shelf temperature was increased to 50° C. The vial was kept at this temperature and a vacuum degree (absolute pressure) of 1.1 Pa for 24 hours.

Example 4

In 800 mL of water for injection, 120.41 g of Compound A was suspended under stirring. Separately, 30.73 g of sodium hydroxide was dissolved in 300 mL of water for injection under stirring. The sodium hydroxide solution was added to the suspension of Compound A. After confirming the dissolution under stirring, 0.2 mol/kg of the sodium hydroxide solution was added to adjust the pH to 8.0. Water for injection was added to raise the total volume to 2000 mL, and the resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 100%

Lyophilization Method

1. The shelf temperature was adjusted to 20° C. and the vial was kept at this temperature for 180 minutes.
2. The shelf temperature was reduced to −47° C. over a period of 41 minutes so as to freeze the content.
3. The vacuum degree (absolute pressure) was set up to 20 Pa and the shelf temperature was increased to 25° C. The vial was kept at this pressure and temperature for 35 hours. The temperature of the frozen product during sublimation of water was −11.9 to −3.0° C.
4. The shelf temperature was increased to 50° C. The vial was kept at this temperature and a vacuum degree (absolute pressure) of 1.1 Pa for 24 hours.

Example 5

In 300 g of water for injection, 42.19 g of Compound A was suspended under stirring. Separately, 10.86 g of sodium hydroxide was dissolved in 299 g of water for injection under stirring. The sodium hydroxide solution was added to the suspension of Compound A. After confirming the dissolution under stirring, 0.2 mol/kg of the sodium hydroxide solution was added to adjust the pH to 8.0. Water for injection was added to raise the total volume to 700 mL, and the resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 100%

Lyophilization Method

1. The shelf temperature was adjusted to 40° C. and the vial was kept at this temperature for 180 minutes.
2. The shelf temperature was reduced to −47° C. over a period of 53 minutes so as to freeze the content.
3. The vacuum degree (absolute pressure) was set up to 20 Pa and the shelf temperature was increased to 0° C. The vial was kept at this pressure and temperature for 66 hours. The temperature of the frozen product during sublimation of water was −5.5° C.
4. The shelf temperature was increased to 50° C. The vial was kept at this temperature and a vacuum degree (absolute pressure) of 1.1 Pa for 20 hours.

Example 6

In 3001 g of water for injection, 422 g of Compound A was suspended under stirring. Separately, 107 g of sodium hydroxide was dissolved in 2501 g of water for injection under stirring. The sodium hydroxide solution was added to the suspension of Compound A. After confirming the dissolution under stirring, 0.2 mol/kg of the sodium hydroxide solution was added to adjust the pH to 8.5. Water for injection was added to raise the total volume to 7 L, and the resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

As the result of the X-ray power diffraction of the obtained lyophilized preparation (good-appearance product), a broad halo pattern, which is specific to amorphous materials, was observed in a low-angle region (20° to 30°). It was confirmed that the lyophilized preparation (good-appearance product) was amorphous.

Yield rate: 99%

Lyophilization Method

1. The shelf temperature was adjusted to 40° C. and the vial was kept at this temperature for 180 minutes.
2. The shelf temperature was reduced to −47° C. over a period of 53 minutes so as to freeze the content.
3. The vacuum degree (absolute pressure) was set up to 20 Pa and the shelf temperature was increased to 30° C. The vial was kept at this pressure and temperature for 27 hours. The temperature of the frozen product during sublimation of water was −15.0 to −7.4° C.
4. The shelf temperature was increased to 50° C. The vial was kept at this temperature and a vacuum degree (absolute pressure) of 1.2 Pa for 23 hours.

Example 7

In 1450 g of water for injection, 181 g of Compound A was suspended under stirring. Separately, 46 g of sodium hydroxide was dissolved in 1100 g of water for injection under stirring. The sodium hydroxide solution was added to the suspension of Compound A. After confirming the dissolution under stirring, 0.2 mol/kg of the sodium hydroxide solution was added to adjust the pH to 7.6. Water for injection was added to raise the total volume to 3 L, and then 750 mL of the resulting mixture was fractionated. Thereto, 0.2 mol/kg of the sodium hydroxide solution was added to adjust the pH to 8.5. The resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 100%

Lyophilization Method

1. The shelf temperature was adjusted to 40° C. and the vial was kept at this temperature for 180 minutes.
2. The shelf temperature was reduced to −47° C. over a period of 53 minutes so as to freeze the content.
3. The vacuum degree (absolute pressure) was set up to 20 Pa and the shelf temperature was increased to 25° C. The vial was kept at this pressure and temperature for 15 hours. The temperature of the frozen product during sublimation of water was −13.7 to −6.0° C.
4. The shelf temperature was increased to 50° C. The vial was kept at this temperature and a vacuum degree (absolute pressure) of 1.1 Pa for 22 hours.

Example 8

In 36 kg of water for injection, 4.518 kg of Compound A was suspended under stirring. Separately, 1.151 kg of sodium hydroxide was dissolved in 10 kg of water for injection under stirring. The sodium hydroxide solution was added to the suspension of Compound A. After confirming the dissolution under stirring, 0.2 mol/kg of the sodium hydroxide solution was added to adjust the pH to 8.0. Water for injection was added to raise the total volume to 77.7 kg, and the resulting mixture was filtered through a 0.22 μm membrane filter (OpticapXL4 Capsule, Merck Ltd.) to obtain a prepared solution.

A vial (V-K 20ML, Fuji Glass Co., Ltd.) was filled with 10 mL of the prepared solution. The filled up vial was half-capped with a rubber stopper (V10-F8W, material D713, coating RB2-40, Daikyo Seiko, Ltd.) and subjected to lyophilization using a lyophilization machine (DFB2000-2MS-ST/CIP, chamber volume: 3.9 m$^3$, specifications for the shelf with five rows, Ulvac, Inc.), followed by sealing of the vial to obtain a lyophilized preparation.

Yield rate: 98%

Lyophilization Method

1. The shelf temperature was adjusted to 40° C. and the vial was kept at this temperature for 180 minutes.
2. The shelf temperature was reduced to −50° C. over a period of 3 hours so as to freeze the content.
3. The vacuum degree (absolute pressure) was set up to 20 Pa and the shelf temperature was increased to 25° C. The vial was kept at this pressure and temperature for 58 hours. The temperature of the frozen product during sublimation of water was −6.0° C.
4. The shelf temperature was increased to 50° C. The vial was kept at this temperature and a vacuum degree (absolute pressure) of 0.5 Pa for 26.5 hours.

Example 9

In 350 mL of water for injection, 42.17 g of Compound A was suspended under stirring. Separately, 10.65 g of sodium hydroxide was dissolved in 250 mL of water for injection under stirring. The sodium hydroxide solution was added to the suspension of Compound A. After confirming the dissolution under stirring, 0.2 mol/kg of the sodium hydroxide solution was added to adjust the pH to 8.5. Water for injection was added to raise the total volume to 700 mL, and the resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 93%

Lyophilization Method

1. The shelf temperature was adjusted to 40° C. and the vial was kept at this temperature for 180 minutes.
2. The shelf temperature was reduced to −47° C. over a period of 3 hours so as to freeze the content.
3. The vacuum degree (absolute pressure) was set up to 20 Pa and the shelf temperature was increased to 25° C. The vial was kept at this pressure and temperature for 35 hours. The temperature of the frozen product during sublimation of water was −5.1 to −4.3° C.
4. The shelf temperature was increased to 50° C. The vial was kept at this temperature and a vacuum degree (absolute pressure) of 1.1 Pa for 24 hours.

Example 10

In 1450 g of water for injection, 181 g of Compound A was suspended under stirring. Separately, 46 g of sodium hydroxide was dissolved in 1100 g of water for injection under stirring. The sodium hydroxide solution was added to the suspension of Compound A. After confirming the dissolution under stirring, 0.2 mol/kg of the sodium hydroxide solution was added to adjust the pH to 7.6. Water for injection was added to raise the total volume to 3 L, and then 750 mL of the resulting mixture was fractionated. Thereto, 0.2 mol/kg of the sodium hydroxide solution was added to adjust the pH to 9.0. The resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 100%

Lyophilization Method

1. The shelf temperature was adjusted to 40° C. and the vial was kept at this temperature for 180 minutes.
2. The shelf temperature was reduced to −47° C. over a period of 53 minutes so as to freeze the content.

3. The vacuum degree (absolute pressure) was set up to 20 Pa and the shelf temperature was increased to 25° C. The vial was kept at this pressure and temperature for 15 hours. The temperature of the frozen product during sublimation of water was −13.7 to −6.0° C.
4. The shelf temperature was increased to 50° C. The vial was kept at this temperature and a vacuum degree (absolute pressure) of 1.1 Pa for 22 hours.

Example 11

In 900 g of water for injection, 120.48 g of Compound A was suspended under stirring. Separately, 30.68 g of sodium hydroxide was dissolved in 700 g of water for injection under stirring. The sodium hydroxide solution was added to the suspension of Compound A. After confirming the dissolution under stirring, 0.2 mol/kg sodium hydroxide solution was added to adjust the pH to 8.0. Water for injection was added to raise the total volume to 2 L. The resulting mixture was filtered through a 0.22 μm membrane filter (Millex-GV, Merck Ltd.) to obtain a prepared solution.

Example 11 (1)

A silicone-coated vial (C0036, TokyoKobunshi Co., Ltd.) was filled with 10 mL of the prepared solution obtained in Example 11. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Example 11 (2)

A silicone-coated vial (271116, Namicos Corporation) was filled with 10 mL of the prepared solution obtained in Example 11. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.
Lyophilization Method in Examples 11 (1) and (2).
1. The shelf temperature was adjusted to 40° C. and the vial was kept at this temperature for 180 minutes.
2. The shelf temperature was reduced to −47° C. over a period of 53 minutes so as to freeze the content.
3. The vacuum degree (absolute pressure) was set up to 20 Pa and the shelf temperature was increased to 25° C. The vial was kept at this pressure and temperature for 33 hours. The temperature of the frozen product during sublimation of water was −15.1 to −8.5° C.
4. The shelf temperature was increased to 50° C. The vial was kept at this temperature and a vacuum degree (absolute pressure) of 1.1 Pa for 23 hours.

It was confirmed that the silicone-coated vials (Examples 11 (1) and (2)) had the same yield rate as that of the non-silicone-coated vial (Example 8). Also, the silicone-coated vials showed no signs of breakage.

Example 12

In 1700 g of water for injection, 150.45 g of Compound A was suspended under stirring. Separately, 38.11 g of sodium hydroxide was dissolved in 500 g of water for injection under stirring. The sodium hydroxide solution was added to the suspension of Compound A. After confirming the dissolution under stirring, 0.2 mol/kg sodium hydroxide solution was added to adjust the pH to 8.0. Water for injection was added to raise the total volume to 2.5 L. The resulting mixture was filtered through a 0.22 μm membrane filter (Millex-GV, Merck Ltd.) to obtain a prepared solution.

10 mL of the prepared solution was filled in a vial (Clear vial 20 ML, SCHOTT AG). The filled up vial was half-capped with a rubber stopper (V10-F8W, Daikyo Seiko, Ltd.) and subjected to lyophilization using a lyophilization machine (DFM-05B-S, Ulvac, Inc.), followed by sealing of the vial to obtain a lyophilized preparation.
Yield rate: 97%
Lyophilization Method
1. The shelf temperature was adjusted to 60° C. and the vial was kept at this temperature for 180 minutes.
2. The shelf temperature was reduced to −47° C. over a period of 45 minutes so as to freeze the content.
3. The vacuum degree (absolute pressure) was set up to 20 Pa and the shelf temperature was increased to 25° C. The vial was kept at this pressure and temperature for 50 hours. The temperature of the frozen product during sublimation of water was −25.6 to −20.1° C.
4. The shelf temperature was increased to 50° C. The vial was kept at this temperature and a vacuum degree (absolute pressure) of 1.0 Pa for 10 hours.

Example 13

In 2500 g of water for injection, 282.07 g of Compound A was suspended under stirring. Separately, 72.08 g of sodium hydroxide was dissolved in 2000 g of water for injection under stirring. The sodium hydroxide solution was added to the suspension of Compound A. After confirming the dissolution under stirring, 0.2 mol/kg sodium hydroxide solution was added to adjust the pH to 8.0. Water for injection was added to raise the total volume to 4.7 L. The resulting mixture was filtered through a 0.22 μm membrane filter (Millex-GV, Merck Ltd.) to obtain a prepared solution.

10 mL of the prepared solution was filled in a vial (Clear vial 20 ML, SCHOTT AG). The filled up vial was half-capped with a rubber stopper (V10-F8W, Daikyo Seiko, Ltd.) and subjected to lyophilization using a lyophilization machine (DFM-05B-S, Ulvac, Inc.), followed by sealing of the vial to obtain a lyophilized preparation.
Yield rate: 97%
Lyophilization Method
1. The shelf temperature was adjusted to 60° C. and the vial was kept at this temperature for 240 minutes.
2. The shelf temperature was reduced to −47° C. over a period of 65 minutes so as to freeze the content.
3. The vacuum degree (absolute pressure) was set up to 20 Pa and the shelf temperature was increased to 0° C. The vial was kept at this pressure and temperature for 100 hours. The temperature of the frozen product during sublimation of water was −25.6 to −16.7° C.
4. The shelf temperature was increased to 50° C. The vial was kept at this temperature and a vacuum degree (absolute pressure) of 1.0 Pa for 6 hours.

Example 14

In 2000 g of water for injection, 270.02 g of Compound A was suspended under stirring. Separately, 68.94 g of sodium hydroxide was dissolved in 2000 g of water for injection under stirring. The sodium hydroxide solution was added to the suspension of Compound A. After confirming the dissolution under stirring, 0.2 mol/kg sodium hydroxide solution was added to adjust the pH to 8.0. Water for injection was added to raise the total volume to 4.5 L. The resulting mixture was filtered through a 0.22 μm membrane filter (Millex-GV, Merck Ltd.) to obtain a prepared solution.

10 mL of the prepared solution was filled in a vial (Clear vial 20 ML, SCHOTT AG). The filled up vial was half-capped with a rubber stopper (V10-F8W, Daikyo Seiko, Ltd.) and subjected to lyophilization using a lyophilization machine (DFM-05B-S, Ulvac, Inc.), followed by sealing of the vial to obtain a lyophilized preparation.

Yield rate: 94%

Lyophilization Method
1. The shelf temperature was adjusted to 60° C. and the vial was kept at this temperature for 180 minutes.
2. The shelf temperature was reduced to −47° C. over a period of 65 minutes so as to freeze the content.
3. The vacuum degree (absolute pressure) was set up to 1.0 Pa and the shelf temperature was increased to 25° C. The vial was kept at this pressure and temperature for 100 hours. The temperature of the frozen product during sublimation of water was −32.5 to −20.6° C.
4. The shelf temperature was increased to 50° C. The vial was kept at this temperature and a vacuum degree (absolute pressure) of 1.0 Pa for 8 hours.

Example 15

In 2000 g of water for injection, 270.02 g of Compound A was suspended under stirring. Separately, 68.94 g of sodium hydroxide was dissolved in 2000 g of water for injection under stirring. The sodium hydroxide solution was added to the suspension of Compound A. After confirming the dissolution under stirring, 0.2 mol/kg sodium hydroxide solution was added to adjust the pH to 8.0. Water for injection was added to raise the total volume to 4.5 L. The resulting mixture was filtered through a 0.22 μm membrane filter (Millex-GV, Merck Ltd.) to obtain a prepared solution.

25 mL of the prepared solution was filled in a vial (Clear vial 50 ML, SCHOTT AG). The filled up vial was half-capped with a rubber stopper (V10-F8W, Daikyo Seiko, Ltd.) and subjected to lyophilization using a lyophilization machine (DFM-05B-S, Ulvac, Inc.), followed by sealing of the vial to obtain a lyophilized preparation.

Yield rate: 96%

Lyophilization Method
1. The shelf temperature was adjusted to 60° C. and the vial was kept at this temperature for 180 minutes.
2. The shelf temperature was reduced to −47° C. over a period of 65 minutes so as to freeze the content.
3. The vacuum degree (absolute pressure) was set up to 1.0 Pa and the shelf temperature was increased to 25° C. The vial was kept at this pressure and temperature for 100 hours. The temperature of the frozen product during sublimation of water was −31.4 to −22.0° C.
4. The shelf temperature was increased to 50° C. The vial was kept at this temperature and a vacuum degree (absolute pressure) of 1.0 Pa for 8 hours.

Comparative Example 1

In 299 g of water for injection, 42.18 g of Compound A was suspended under stirring. Separately, 10.59 g of sodium hydroxide was dissolved in 293 g of water for injection under stirring. The sodium hydroxide solution was added to the suspension of Compound A. After confirming the dissolution under stirring, 0.2 mol/kg of the sodium hydroxide solution was added to adjust the pH to 8.0. Water for injection was added to raise the total volume to 700 mL, and the resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 82%

Lyophilization Method
1. The shelf temperature was adjusted to 5° C. and the vial was kept at this temperature for 180 minutes.
2. The shelf temperature was reduced to −47° C. over a period of 53 minutes so as to freeze the content.
3. The vacuum degree (absolute pressure) was set up to 20 Pa and the shelf temperature was increased to 25° C. The vial was kept at this pressure and temperature for 35 hours. The temperature of the frozen product during sublimation of water was −6.1° C.
4. The shelf temperature was increased to 50° C. The vial was kept at this temperature and a vacuum degree (absolute pressure) of 1.1 Pa for 24 hours.

Comparative Example 2

In 300 mL of water for injection, 42.25 g of Compound A was suspended under stirring. Separately, 10.47 g of sodium hydroxide was dissolved in 300 mL of water for injection under stirring. The sodium hydroxide solution was added to the suspension of Compound A. After confirming the dissolution under stirring, 0.2 mol/kg of the sodium hydroxide solution was added to adjust the pH to 8.0. Water for injection was added to raise the total volume to 700 mL, and the resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 53%

Lyophilization Method
1. The shelf temperature was adjusted to 30° C. and the vial was kept at this temperature for 180 minutes.
2. The shelf temperature was reduced to −47° C. over a period of 3 hours so as to freeze the content.
3. The vacuum degree (absolute pressure) was set up to 20 Pa and the shelf temperature was increased to 25° C. The vial was kept at this pressure and temperature for 34 hours. The temperature of the frozen product during sublimation of water was −9.9 to −6.3° C.
4. The shelf temperature was increased to 50° C. The vial was kept at this temperature and a vacuum degree (absolute pressure) of 1.1 Pa for 4 hours.

Comparative Example 3

In 350 mL of water for injection, 42.20 g of Compound A was suspended under stirring. Separately, 10.73 g of sodium hydroxide was dissolved in 250 mL of water for injection under stirring. The sodium hydroxide solution was added to the suspension of Compound A. After confirming the dissolution under stirring, 0.2 mol/kg of the sodium hydroxide solution was added to adjust the pH to 8.0. Water for injection was added to raise the total volume to 700 mL, and the resulting mixture was filtered through a 0.22 μm membrane filter (Millex-GV, Merck Ltd.) to obtain a prepared solution.

A vial (V-K 20ML, Fuji Glass Co., Ltd.) was filled with 10 mL of the prepared solution. The filled up vial was half-capped with a rubber stopper (F10-91-3, Sumitomo Rubber Industries, Ltd.) and subjected to lyophilization using a lyophilization machine (DFM-05B-S, Ulvac, Inc.), followed by sealing of the vial to obtain a lyophilized preparation.

Yield rate: 73%

Lyophilization Method

1. The shelf temperature was adjusted to 20° C. and the vial was kept at this temperature for 180 minutes.
2. The shelf temperature was reduced to −47° C. over a period of 3 hours so as to freeze the content.
3. The vacuum degree (absolute pressure) was set up to 20 Pa and the shelf temperature was increased to 25° C. The vial was kept at this pressure and temperature for 35 hours. The temperature of the frozen product during sublimation of water was −16.7 to −6.0° C.
4. The shelf temperature was increased to 50° C. The vial was kept at this temperature and a vacuum degree (absolute pressure) of 1.2 Pa for 24 hours.

using a lyophilization machine (DFM-05B-S, Ulvac, Inc.), followed by sealing of the vial to obtain a lyophilized preparation.

As the result of the X-ray power diffraction of the obtained lyophilized preparation (good-appearance product), a broad halo pattern, which is specific to amorphous materials, was observed in a low-angle region (20° to 30°). It was confirmed that the lyophilized preparation (good-appearance product) was amorphous.

Yield rate: 72%

Lyophilization Method

1. The shelf temperature was reduced from 25° C. to −45° C. over a period of 2 hours so as to freeze the content.
2. The vacuum degree (absolute pressure) was set up to 1.1 Pa and the shelf temperature was increased to 40° C. The vial was kept at this pressure and temperature for 53 hours. The temperature of the frozen product during sublimation of water was −13.1 to −2.2° C.

Figure 1:
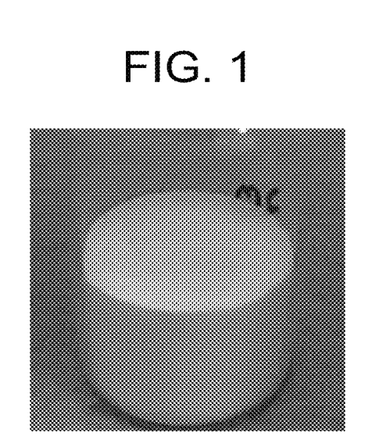
FIG. 1 is a photograph of a good-appearance product (a lyophilized preparation having a yellow to light yellow appearance and showing no white part).
Figure 2:
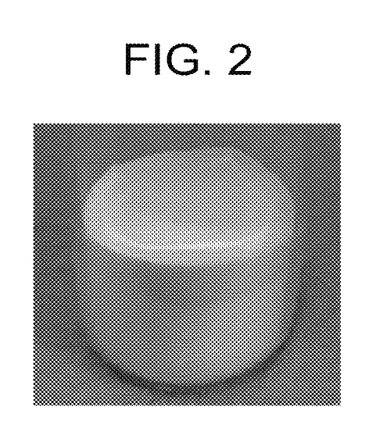
FIG. 2 is a photograph of a poor-appearance product (a lyophilized preparation showing a white part).

The production conditions and yield rates of the examples and the comparative examples are shown in Table 1. FIG. 1 shows a photograph of a good-appearance product and FIG. 2 shows a photograph of a poor-appearance product.

TABLE 1

| | Freezing conditions Cooling start temperature- Cooling time | Primary drying conditions Shelf temperature- Vacuum degree | Temperature of the frozen product during sublimation of moisture | Yield rate (%) |
|---|---|---|---|---|
| Example 1 | 50° C.-53 min | 25° C.-20 Pa | −13.2~−3.3° C. | 100 |
| Example 2 | 40° C.-53 min | 25° C.-20 Pa | −13.7~−6.0° C. | 100 |
| Example 3 | 30° C.-53 min | 25° C.-20 Pa | −6.1° C. | 100 |
| Example 4 | 20° C.-41 min | 25° C.-20 Pa | −11.9~−3.0° C. | 100 |
| Example 5 | 40° C.-53 min | 0° C.-20 Pa | −5.5° C. | 100 |
| Example 6 | 40° C.-53 min | 30° C.-20 Pa | −15.0~−7.4° C. | 99 |
| Example 7 | 40° C.-53 min | 25° C.-20 Pa | −13.7~−6.0° C. | 100 |
| Example 8 | 40° C.-3 hr | 25° C.-20 Pa | −6.0° C. | 98 |
| Example 9 | 40° C.-3 hr | 25° C.-20 Pa | −5.1~−4.3° C. | 93 |
| Example 10 | 40° C.-53 min | 25° C.-20 Pa | −13.7~−6.0° C. | 100 |
| Example 11(1) | 40° C.-53 min | 25° C.-20 Pa | −15.1~−8.5° C. | 99 |
| Example 11(2) | 40° C.-53 min | 25° C.-20 Pa | −15.1~−8.5° C. | 99 |
| Example 12 | 60° C.-45 min | 25° C.-20 Pa | −25.6~−20.1° C. | 97 |
| Example 13 | 60° C.-65 min | 0° C.-20 Pa | −25.6~−16.7° C. | 97 |
| Example 14 | 60° C.-65 min | 25° C.-1.0 Pa | −32.5~−20.6° C. | 94 |
| Example 15 | 60° C.-65 min | 25° C.-1.0 Pa | −31.4~−22.0° C. | 96 |
| Comparative Example 1 | 5° C.-53 min | 25° C.-20 Pa | −6.1° C. | 82 |
| Comparative Example 2 | 30° C.-3 hr | 25° C.-20 Pa | −9.9~−6.3° C. | 53 |
| Comparative Example 3 | 20° C.-3 hr | 25° C.-20 Pa | −16.7~−6.0° C. | 73 |
| Comparative Example 4 | 25° C.-2 hr | 40° C. 1.1 Pa | −13.1~−2.2° C. | 72 |

Comparative Example 4

In 346 g of water for injection, 60 g of Compound A was suspended under stirring. 198 g of 2 mol/L of the sodium hydroxide solution was added to the suspension of Compound A. After confirming the dissolution under stirring, 0.2 mol/kg of the sodium hydroxide solution was added to adjust the pH to 8.1. Water for injection was added to raise the total volume to 800 mL, and the resulting mixture was filtered through a 0.22 μm membrane filter (Millex-GV, Merck Ltd.) to obtain a prepared solution.

A vial (V-K 20ML, Fuji Glass Co., Ltd.) was filled with 8 mL of the prepared solution. The filled up vial was half-capped with a rubber stopper (F10-91-3, Sumitomo Rubber Industries, Ltd.) and subjected to lyophilization Test Example 1

The lyophilized preparations with which the normal vial obtained in Example 8 and the silicone-coated vials obtained in Examples 11 (1) and (2) were subjected to a stability test. The stability test was conducted for the following evaluation items under the following evaluation conditions:

Evaluation items: Analog substances, pH, re-solubility, and moisture

Evaluation condition: Temperature: 40° C.; Duration: Maximum 6 months

Test results: The test results of the stability test are shown in Table 2.

Regardless of the presence or absence of the silicone coating, each evaluation item was within the target range. It was confirmed that the silicone-coated vials have the same degree of stability as the non-silicone-coated vial.

TABLE 2

| Examples | Silicone-coating manufacturers | Storage conditions | | Total analogs (%) | pH | Re-solubilization (Sec.) | Moisture (%) |
|---|---|---|---|---|---|---|---|
| Examples 11(1) | TokyoKobunshi Co., Ltd. | Start | | 0.10 | 8.3 | 65 | 0.2 |
| | | 40° C. | 3 M | 0.08 | 8.3 | 80 | 0.3 |
| | | | 6 M | 0.14 | 8.2 | 75 | 0.4 |
| Examples 11(2) | Namicos Corporation | Start | | 0.11 | 8.3 | 55 | 0.3 |
| | | 40° C. | 3 M | 0.08 | 8.3 | 75 | 0.3 |
| | | | 6 M | 0.16 | 8.2 | 60 | 0.4 |
| Examples 8 | None | Start | | 0.07 | 8.3 | 52 | 0.1 |
| | | 40° C. | 3 M | 0.09 | 8.3 | 52 | 0.2 |
| | | | 6 M | 0.09 | 8.2 | 57 | 0.2 |
| | Target value | | | <1.0 | 7.5-9.0 | — | <0.6 |

INDUSTRIAL APPLICABILITY

The method of producing a lyophilized preparation containing amorphous Salt A of the present invention can perform scale-up and is useful as a method of producing a uniform quality of lyophilized preparation.

The invention claimed is:

1. A method of producing a lyophilized preparation comprising amorphous sodium salt of 6-fluoro-3-hydroxy-2-pyrazine carboxamide, the method comprising:
   (1) adjusting the temperature of an aqueous solution comprising a sodium salt of 6-fluoro-3-hydroxy-2-pyrazine carboxamide to 20° C. or more;
   (2) cooling the aqueous solution obtained in the adjusting (1) to −40° C. or less within 1 hour to produce a frozen product; and
   (3) lyophilizing the frozen product obtained in the cooling (2).

2. The production method according to claim 1, wherein the temperature in the adjusting (1) is in a range of 20° C. or more and less than 30° C.

3. The production method according to claim 1, wherein the temperature in the adjusting (1) is in a range of 30° C. or more and less than 40° C.

4. The production method according to claim 1, wherein the temperature in the adjusting (1) is in a range of 40° C. or more and less than 50° C.

5. The production method according to claim 1, wherein the temperature in the adjusting (1) is in a range of 50° C. or more and less than 60° C.

6. The production method according to claim 1, wherein the temperature in the adjusting (1) is in a range of 60° C. or more and less than 70° C.

7. The production method according to claim 1, wherein the temperature of the frozen product during sublimation of water in a primary drying of the lyophilizing (3) is in a range of −30° C. or more and less than 0° C., and the vacuum degree (absolute pressure) is in a range of 15 Pa or more and less than 25 Pa.

8. The production method according to claim 1, wherein the temperature of the frozen product during sublimation of water in a primary drying of the lyophilizing (3) is in a range of −40° C. or more and less than −15° C.

9. A method of producing a lyophilized preparation comprising amorphous sodium salt of 6-fluoro-3-hydroxy-2-pyrazine carboxamide, the method comprising:
   (1) adjusting the temperature of an aqueous solution comprising a sodium salt of 6-fluoro-3-hydroxy-2-pyrazine carboxamide to 40° C. or more;
   (2) cooling the aqueous solution obtained in the adjusting (1) to −40° C. or less within 3 hours to produce a frozen product; and
   (3) lyophilizing the frozen product obtained in the cooling (2).

10. The production method according to claim 9, wherein the temperature in the adjusting (1) is in a range of 40° C. or more and less than 50° C.

11. The production method according to claim 9, wherein the temperature in the adjusting (1) is in a range of 50° C. or more and less than 60° C.

12. The production method according to claim 9, wherein the temperature in the adjusting (1) is in a range of 60° C. or more and less than 70° C.

* * * * *